United States Patent [19]

Sawicki

[11] Patent Number: 4,575,561

[45] Date of Patent: Mar. 11, 1986

[54] CARBOXYALKYLATION OF ARYL-SUBSTITUTED ALKYL HALIDES TO THE CORRESPONDING ESTERS

[75] Inventor: Robert A. Sawicki, Wappingers Falls, N.Y.

[73] Assignee: Texaco Inc., White Plains, N.Y.

[21] Appl. No.: 479,592

[22] Filed: Mar. 28, 1983

[51] Int. Cl.$^4$ ................................................ C07C 69/76
[52] U.S. Cl. ..................................... 560/105; 562/406
[58] Field of Search ................. 562/406; 560/105, 519

[56] References Cited

U.S. PATENT DOCUMENTS 3,116,306 12/1963 Heck et al. ............................ 562/406
3,928,429 12/1971 El-Chahawi et al. ................ 562/406

Primary Examiner—Paul J. Killos
Attorney, Agent, or Firm—Robert A. Kulason; Carl G. Seutter

[57] ABSTRACT

Aryl-substituted acetic acid esters are directly prepared by carbonylation of benzyl halides under one atmosphere of carbon monoxide at ambient temperature in alcohol solvent using as catalyst dicobalt octacarbonyl and a base-alumina as co-reactant.

14 Claims, No Drawings

CARBOXYALKYLATION OF ARYL-SUBSTITUTED ALKYL HALIDES TO THE CORRESPONDING ESTERS

FIELD OF THE INVENTION

This invention relates to the direct preparation of esters of organic acids. More particularly it relates to the preparation of esters of phenylacetic acid.

BACKGROUND OF THE INVENTION

Arylacetic acids and esters are widely used in the chemical industry as intermediates for many products. Phenylacetic acid in particular may be prepared by the conversion of benzyl chloride to the cyanide which, upon hydrolysis, is converted to the acid which may be converted to the desired ester. This process, however, is undesirable inter alia in that it is characterized by danger to personnel who must utilize special precautions when handling cyanides.

Other approaches to the preparation of phenylacetic acid (U.S. Pat. No. 3,708,529) include the carbonylation of benzyl chloride at 20° C.–80° C. and atmospheric pressure utilizing a catalyst mixture containing (i) a cobalt salt such as $CoCl_2$, (ii) an iron-manganese alloy, and (iii) a sulphurated promoting agent such as sodium thiosulfate.

U.S. Pat. No. 3,928,429 discloses a similar reaction at 30° C.–70° C. in the presence of a cobalt or iron carbonyl plus water and an alcohol.

U.S. Pat. No. 4,034,004 discloses use of a catalyst system containing (i) a palladium or phosphine-palladium component, and (ii) a quaternary alkyl ammonium salt—typically tetrabutyl ammonium iodide and $Pd[P(C_6H_5)_3]_4 \cdot P(C_6H_5)_3$.

U.S. Pat. No. 4,128,572 discloses use, in diphase system, of catalyst system containing (i) a quaternary alkylammonium salt and a cobalt hydrocarbonyl salt.

Prior art techniques yield little or no ester product and if the ester is the desired product, it is necessary to separately esterify the acid.

It is an object of this invention to provide a process for direct preparation of esters of acids such as phenylacetic acid. Other objects will be apparent to those skilled in the art.

STATEMENT OF THE INVENTION

In accordance with certain of its aspects, this invention is directed to a method which comprises
carbonylating $R'CH_2X$, wherein X is an active halide and R' is an aromatic hydrocarbon group at 0° C.–75° C. and at a carbon monoxide partial pressure of 760–1,500 mm Hg in liquid phase in the presence of ROH, wherein R is alkyl, alkenyl, alkynyl, alkaryl, aralkyl, cycloalkyl or aryl in the presence of catalyst composition containing as catalyst a cobalt carbonyl and as a co-reactant a base-alumina or base-silica thereby forming product stream containing ester; and
recovering said product stream containing ester.

DESCRIPTION OF THE INVENTION

The charge compounds which may be employed in practice of the process of this invention may be represented by the formula $R'CH_2X$ wherein R' is an aromatic hydrocarbon group such as an aryl group, an alkaryl group, etc. typified by tolyl, xylyl, or more preferably phenyl, and X is an active halide, typified by chlorine, bromine, or iodine. The preferred charge compound may be benzyl bromide.

Conversion of charge halide to product may be in accordance with the following equation:

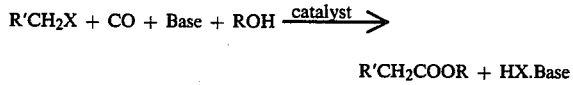

$$R'CH_2X + CO + \text{Base} + ROH \xrightarrow{\text{catalyst}}$$
$$R'CH_2COOR + HX \cdot \text{Base}$$

The catalyst composition may include as catalyst a cobalt carbonyl, preferably dicobalt octacarbonyl catalyst and as a co-reactant a base-alumina or base-silica. In a preferred embodiment, the system may include as co-reactant a base-alumina, i.e. an alumina which has been made basic by addition thereto of a base.

It is a feature of this invention that the co-reactant preferably includes an alumina-base composition. These basic alumina composition may be prepared from alumina $Al_2O_3$; any of the various forms of alumina may be employed including gamma alumina, eta alumina, beta alumina, etc.; aluminum hydroxide, etc. When the co-reactant is a base-silica, it may be prepared from a silica such as silica gel.

Formation of the co-reactant is effected by adding a base to the alumina or silica. Typical bases may include hydroxides such as potassium hydroxide, sodium hydroxide, etc; alkoxides such as potassium methoxide, potassium propoxide, potassium t-butoxide, etc.; carbonates such as sodium carbonate, potassium carbonate, etc.

Formation of the co-reactant may be carried out at 25° C.–200° C., say 25° C., by adding 0.5–1.5 moles, say 0.98 moles of alumina and 0.2–1.0 moles, say 0.4 moles of base to 50–500 ml, say 200 ml of solvent. The preferred solvent is water for the metal hydroxides and carbonate bases and alcohol for the alkoxide bases. The solvent is then stripped under vacuum, typically 1.5 mm Hg at 75° C. for one hour and then at 175° C. for one hour. The resulting powder is used in the carbonylation reaction.

The co-reactant contains 0.2–0.8 molar parts, say 0.4 molar parts of base per 100 parts of alumina or silica. A preferred co-reactant contains 0.43 moles (30 g) of potassium methoxide on 100 g of alumina.

Metal carbonyl catalysts may be employed typified by carbonyls of cobalt. Illustrative of these compositions are $Co_2(CO)_8$. The catalyst—preferably dicobalt octacarbonyl—is preferably added in amount of 0.001–1 moles, say 0.01 moles. The mole ratio of catalyst:co-reactant may be 0.001:1–0.1:1 preferably 0.02:1.

Charge halide $R'CH_2X$, typically benzyl bromide (0.01–1 moles, say 0.025 moles) is added slowly to the reaction mixture over 5–120 minutes, say 60 minutes; and thereafter the reaction mixture is maintained at 0° C.–50° C.; say 25° C. for 1–48 hours, say 24 hours. During the entire course of the reaction, the reaction mixture is maintained under a carbon monoxide pressure of 760–1500 mm Hg, say 760 mm Hg. The reaction solvent may preferably be a lower $C_1$–$C_8$ alkanol, preferably methanol.

It is preferred that the reaction mixture be substantially anhydrous; i.e. containing less than about 0.1 w % water. Although no water is normally added to the reaction mixture, the presence of small amounts such as may be found in, e.g., commercial alcohols, etc. does not appear to be significantly detrimental.

During reaction, the charge halide typically is carbonylated to directly form, in the presence of alcohol the desired product ester R'CH$_2$COOR.

The ester may be separated by distillation.

Typically ester may be recovered in yield of 22%–70%, say 70% (for the preferred potassium methoxide on alumina catalyst). It is a feature of the process of this invention in its preferred embodiments that the selectivity to ester may approach 100%.

Ester products which may be prepared by the process of this invention may include:

TABLE methyl phenylacetate
ethyl phenylacetate
n-butyl phenylacetate
methyl o-tolylacetate
methyl m-tolylacetate
methyl p-tolylacetate It is a feature of the process of this invention that it is possible to directly prepare product esters in high selectivity and yield at ambient temperature. Reaction at room temperature may permit attainment of product in yield of 70% or more and at selectivity of 85% or higher.

DESCRIPTION OF THE PREFERRED EMBODIMENTS

Practice of the process of this invention will be apparent to those skilled in the art from the following examples wherein, as elsewhere in this specification, all parts are parts by weight unless otherwise specified. Control examples are shown with an asterisk.

PREPARATION OF BASE-ALUMINA CO-REACTANT

EXAMPLE I

Sodium Hydroxide on Alumina

A mixture containing 16 g (0.40 mol) sodium hydroxide, 100 g alumina, and 200 ml water was placed in a 500 ml flask. The solvent was stripped under vacuum on a rotary evaporator (one hour at 75° C. then one hour at 175° C.) leaving 112 g of a white powder.

EXAMPLE II

Potassium Methoxide on Alumina

A mixture containing 30 g (0.43 mol) potassium methoxide, 200 ml methanol and 100 g alumina was stripped of solvent as in Example I. A white powder (127 g) was obtained.

EXAMPLE III

Sodium Ethoxide on Alumina

A mixture containing 28 g (0.41 mol) sodium ethoxide, 200 ml ethanol, and 100 g alumina was stripped of solvent as in Example I. A tan powder (119 g) was obtained.

EXAMPLE IV

Potassium t-Butoxide on Alumina

A mixture containing 45 g (0.40 mol) potassium t-butoxide, 200 ml t-butyl alcohol, and 100 g alumina was stripped of solvent as in Example I leaving 122 g of a white powder.

EXAMPLE V

Sodium Carbonate on Alumina

A mixture containing 21.2 g (0.20 mol) sodium carbonate, 100 ml water, and 50 g alumina was stripped of solvent as in Example I leaving 71 g of a white powder.

EXAMPLE VI

Sodium Isobutoxide on Alumina

A mixture containing 2.1 g(0.05 mol) sodium hydroxide, 50 ml isobutyl alcohol, and 13 g alumina was heated at reflux for 1½ hours removing the trace water azeotrope. The resulting hetergeneous mixture was used as the co-reactant.

EXAMPLE VII

Potassium Methoxide on Silica Gel

A mixture containing 30 g (0.43 mol) potassium methoxide, 200 ml methanol and 100 g silica gel was stripped of solvent as in Example I leaving a white powder.

EXAMPLE VIII*

Preparation of Methyl Phenylacetate

Into a 100 ml ice-bath cooled flask fitted with a magnetic stirrer, reflux condenser, and addition funnel was added 50 ml methanol, 15 g alumina, and 0.321 g (0.94 mmol) dicobalt octacarbonyl. Benzyl bromide (4.3 g, 25 mmol) in 25 ml methanol was added to the pot over 30 minutes under one atmosphere pressure carbon monoxide. The resulting mixture was stirred 25 hours at room temperature under CO. After filtering, the resulting crude product mixture was analyzed by gas chromatography and shown to give less than 5% yield of methyl phenylacetate using nonane as an internal standard.

EXAMPLE IX*

Procedure and workup were identical to Example VIII using methanol, 3.7 g (52.7 mmol) potassium methoxide, 0.367 g (1.07 mmol) dicobalt octacarbonyl, and 4.3 g (25 mmol) benzyl bromide (and no alumina). The crude product mixture showed less than 5% yield methyl phenylacetate.

EXAMPLE X

Procedure and workup were identical to Example VIII using methanol, 3.7 g (52.7) mmol) potassium methoxide, and 11.3 g alumina that had been dried under vacuum at 175° C. for one hour, 0.371 g (1.08 mmol) dicobalt octacarbonyl, and 4.3 g (25 mmol) benzyl bromide. The crude product mixture contained 20% methyl phenylacetate.

EXAMPLE XI*

Procedure and workup were identical to Example VIII using methanol, 5.3 g (52.4 mmol) triethylamine, 0.313 g (0.92 mmol) dicobalt octacarbonyl, and 4.3 g (25 mmol) benzyl bromide. The crude product mixture contained 15% yield methyl phenylacetate.

EXAMPLE XII

The procedure was identical to Example VIII using methanol, 15 g (50 mmol) of the product of Example I, 0.316 g (0.92 mmol) dicobalt octacarbonyl, and 4.3 g (25 mmol) benzyl bromide. The crude product mixture contained 46% yield methyl phenylacetate and 31% yield phenylacetic acid. The acid was isolated by extraction of the resulting filtrate with base, followed by neutralization with hydrochloric acid, extraction with methylene chloride, and stripping of solvent to afford phenylacetic acid as white crystals.

EXAMPLE XIII

Procedure and workup were identical to Example VIII using methanol, 15 g (50 mmol) of the base-alumina of Example II, 0.341 g (1.0 mmol) dicobalt octacarbonyl, and 4.3 g (25 mmol) benzyl bromide. The crude product mixture contained 70% yield methyl phenylacetate.

EXAMPLE XIV

Procedure and workup were identical to Example VIII using methanol, 15 g (50 mmol) of the base-alumina of Example III, 0.314 g (0.92 mmol) dicobalt octacarbonyl, and 4.3 g (25 mmol) benzyl bromide. The crude product mixture contained 65% yield methyl phenylacetate.

EXAMPLE XV

Procedure and workup were identical to Example VIII using methanol, 15 g (50 mmol) of the base-alumina of Example IV, 0.325 (0.95 mmol) dicobalt octacarbonyl, and 4.3 g (25 mmol) benzyl bromide. The crude product mixture contained 22% yield methyl phenylacetate.

EXAMPLE XVI

Procedure and workup were identical to Example VIII using methanol, 15 g (50 mmol) of the base-alumina of Example V, 0.334 g (0.98 mmol) dicobalt octacarbonyl and 4.3 g (25 mmol) benzyl bromide. The crude product mixture contained 32% yield methyl phenylacetate.

EXAMPLE XVII

Procedure and workup were identical to Example VIII using methanol, 15 g (50 mmol) of the base-alumina of Example II, 0.328 g (0.96 mmol) dicobalt octacarbonyl, and 3.2 g (25 mmol) benzyl chloride. The crude product mixture contained 57% yield methyl phenylacetate.

EXAMPLE XVIII

Procedure and workup were identical to Example VIII using methanol, 15 g (50 mmol) of the base-alumina of Example VII, 0.313 g (0.92 mmol) dicobalt octacarbonyl, and 4.3 g (25 mmol) benzyl bromide. The crude product mixture contained 17% yield of methyl phenylacetate.

EXAMPLE XIX

Procedure and workup were identical to Example VIII using 75 ml isobutanol, 15 g of the base-alumina of Example VI (50 mmol), 0.306 g (0.89 mmol) dicobalt octacarbonyl, and 4.3 g (25 mmol) benzyl bromide. The crude product mixture contained 67% yield of isobutyl phenylacetate.

EXAMPLE XX

Procedure and workup were identical to Example VIII using 75 ml isobutanol, 15 g (50 mmol) of the base-alumina of Example II, 0.329 g (0.96 mmol) dicobalt octacarbonyl, and 4.3 g (25 mmol) benzyl bromide. The crude product mixture contained 26% yield of isobutyl phenylacetate.

EXAMPLE XXI

Procedure and workup were identical to Example XII using methanol, 15 g (50 mmol) of the base-alumina of Example I, 0.317 g (0.93 mmol) dicobalt octacarbonyl, and 3.2 g (25 mmol) benzyl chloride. The crude product mixture contained 46% yield methyl phenylacetate.

In summary, the co-reactants include the following

TABLE

| Example | Co-Reactant |
|---|---|
| I | $NaOH/Al_2O_3$ |
| II | $CH_3OK/Al_2O_3$ |
| III | $CH_3CH_2ONa/Al_2O_3$ |
| IV | $(CH_3)_3C-OK/Al_2O_3$ |
| V | $Na_2CO_3/Al_2O_3$ |
| VI | $CH_3-CH(CH_3)CH_2ONa/Al_2O_3$ |
| VII | $CH_3OK/SiO_2$ |

In summary, the product esters for Examples VIII–XXI are as follows:

TABLE

| Example | Charge Halide | Co-Reactant | Yield Ester Product % |
|---|---|---|---|
| VIII* | $PhCH_2Br$ | $Al_2O_3$ | 5 |
| IX* | $PhCH_2Br$ | MeOK | 5 |
| X | $PhCH_2Br$ | $MeOK/Al_2O_3$ | 20 |
| XI* | $PhCH_2Br$ | $Et_3N$ | 15 |
| XII | $PhCH_2Br$ | I | 46 |
| XIII | $PhCH_2Br$ | II | 70 |
| XIV | $PhCH_2Br$ | III | 65 |
| XV | $PhCH_2Br$ | IV | 22 |
| XVI | $PhCH_2Br$ | V | 32 |
| XVII | $PhCH_2Cl$ | II | 57 |
| XVIII | $PhCH_2Br$ | VII | 17 |
| XIX | $PhCH_2Br$ | VI | 67 |
| XX | $PhCH_2Br$ | II | 26 |
| XXI | $PhCH_2Cl$ | I | 46 |

The results from the Table indicate that both base and alumina are required to obtain high yields of ester products.

Although this invention has been illustrated by reference to specific embodiments, it will be apparent to those skilled in the art that various changes and modifications may be made which clearly fall within the scope of this invention.

I claim:
1. The method which comprises
   carbonylating $R'CH_2X$, wherein X is an active halide and $R'$ is an aromatic hydrocarbon group at 0° C.–50° C. and at a carbon monoxide partial pressure of 760–1500 mm Hg in liquid phase in the presence of ROH, wherein R is alkyl, alkenyl, alkynyl, alkaryl, aralkyl, cycloalkyl or aryl in the presence of catalyst composition containing as catalyst a cobalt carbonyl and as a co-reactant a base-alumina or base-silica thereby forming product stream; and recovering said product stream.

2. The method as claimed in claim 1 wherein said catalyst is dicobalt octacarbonyl.

3. The method as claimed in claim 1 wherein R' is phenyl.

4. The method as claimed in claim 1 wherein R'CH$_2$X is benzyl chloride or benzyl bromide.

5. The method as claimed in claim 1 wherein said reaction is carried out at ambient temperature.

6. The method as claimed in claim 1 wherein said reaction is carried out at atmospheric pressure.

7. The method as claimed in claim 1 wherein ROH is a lower alkanol.

8. The method as claimed in claim 1 wherein ROH is methanol or isobutanol.

9. The method as claimed in claim 1 wherein said base is an inorganic base selected from the group consisting of oxides, hydroxides, alkoxides, and carbonates of alkali metals.

10. The method as claimed in claim 1 wherein said base is sodium hydroxide or potassium hydroxide.

11. The method is claimed in claim 1 wherein said base is potassium methoxide.

12. The method is claimed in claim 1 wherein said base is sodium ethoxide.

13. The method is claimed in claim 1 wherein said base is sodium isobutoxide.

14. The method which comprises
carbonylating R'CH$_2$X wherein X is an active halide and R' is an aromatic hydrocarbon group at 0° C.-50° C. and at a carbon monoxide partial pressure of 760-1500mm Hg in liquid phase in the presence of alcohol ROH wherein R is alkyl, alkenyl, alkynyl, alkaryl, aralkyl, cycloalkyl, or aryl in the presence of catalyst composition containing dicobalt octacarbonyl catalyst and as co-reactant a potassium methoxide on alumina thereby forming product stream containing ester R'CH$_2$COOR; and recovering said product stream.

* * * * *